United States Patent [19]

Tutsky

[11] Patent Number: 4,784,849

[45] Date of Patent: Nov. 15, 1988

[54] SKIN CARE AND SHAVING COMPOSITIONS

[76] Inventor: Ronald J. Tutsky, P.O. Box 1646, Greenwich, Conn. 06836-1646

[21] Appl. No.: 10,388

[22] Filed: Feb. 3, 1987

Related U.S. Application Data

[60] Division of Ser. No. 743,203, Jun. 10, 1985, abandoned, which is a continuation of Ser. No. 523,003, Aug. 15, 1983, Pat. No. 4,525,344.

[51] Int. Cl.$^4$ .......................... A61K 7/15; A61K 7/48; A61K 9/07
[52] U.S. Cl. ...................................... 424/73; 514/847; 514/873; 514/969
[58] Field of Search .................. 514/873, 969, 847; 424/73

[56] References Cited

U.S. PATENT DOCUMENTS

| | | | |
|---|---|---|---|
| 2,532,206 | 11/1950 | Taub et al. ...................... | 514/969 X |
| 4,046,874 | 9/1977 | Gabby et al. ..................... | 424/73 |
| 4,332,763 | 6/1982 | Hempel et al. ................... | 424/63 |
| 4,427,670 | 1/1984 | Ofuchi et al. .................... | 514/969 |

FOREIGN PATENT DOCUMENTS

| | | | |
|---|---|---|---|
| 0024161 | 2/1981 | European Pat. Off. ............ | 424/73 |
| 1051575 | 9/1953 | France ............................. | 424/73 |
| 0088304 | 5/1983 | Japan ............................... | 514/873 |
| 2066071 | 7/1981 | United Kingdom .............. | 514/841 |
| 2095996 | 10/1982 | United Kingdom .............. | 514/841 |

OTHER PUBLICATIONS

Cosmetics & Toiletries, 4/1980, vol. 95; pp. 106, 108 and 116.
Bennett, The Cosmetic Formulary, 1937, pp. 32, 38, 39, 58, 68.

*Primary Examiner*—Dale R. Ore
*Attorney, Agent, or Firm*—Steele, Gould & Fried

[57] ABSTRACT

A combination skin care and shaving composition which essentially contains a phospholipid, wheat germ oil and vitamin E that prevents pseudo folliculitis.

4 Claims, No Drawings

SKIN CARE AND SHAVING COMPOSITIONS

This is a continuation-in-part of application Ser. No. 743,203, filed June 10, 1985, now abandoned, which is a continuation of Ser. No. 523,003, filed 8/15/83, now U.S. Pat. No. 4,525,344.

FIELD OF THE INVENTION

The present invention relates to novel skin conditioning compositions which can be utilized as shaving preparations. More particularly, the present invention relates to a shaving preparation which can be utilized with or without soap and water, and which provides the skin with a protective coating so as to avoid nicks during shaving. Additionally, the invention relates to novel shaving compositions which avoids pseudo folliculitis.

DESCRIPTION OF THE PRIOR ART

The treatment of human skin with various agents has been undertaken for many years with the goal being to keep the skin in a smooth supple condition. Skin has the tendency to dry out when exposed to conditions of low humidity or to extended periods in detergent. These considerations have never been taken to mind when shaving preparations are proposed.

Sagarin, *Cosmetics, Science and Technology*, 2nd Edition, Vol. 1, Wiley Interscience (1972) has been recommended for applications for the skin. There is disclosed some of the ingredients of the current invention but not in the critical combination or for use as a preparation.

Shaving lotions have generally been prepared with regard to the hair follicles only so as to prepare a beard for cutting by a razor. Silicone products have been introduced in order that a razor may travel more easily on the skin without nicking. None of the products provide any beneficial features to the skin. In fact, most commercial products contain ingredients which cause denaturization or other harmful effects. Shaving preparations containing detergents or soap products or one of such deleterious products, are commonly utilized today. It is only after the shaving process that any concern is made for conditioning the skin.

SUMMARY OF THE INVENTION

It is an object of the present invention to provide a skin care preparation.

It is a further object of the present invention to provide a skin care preparation which can be utilized as a shaving composition.

It is a yet still further object of the invention to provide a shaving composition and method which helps to avoid pseudo folliculitis.

Another object of the invention is to provide a shaving composition which not only facilitates shaving but provides beneficial effects to the skin whether or not shaving is required.

Yet another object of the present invention is to provide a shaving preparation which simultaneously conditions the skin, prepares the hair follicles for shaving and provides an effective barrier so as to permit the razor to glide across the skin without causing nicks.

A still further object of the invention is to provide a skin care preparation which provides beneficial effects to the skin when utilized in a stem room or sauna and permits shaving without utilizing any soap or water.

These and other objectives of the invention are obtained by utilizing a skin conditioning and beard conditioning composition which contains a combination of ingredients wherein some ingredients penetrate into the skin, some ingredients penetrate and set up the beard and other ingredients which act on the skin surface as a moisturizing agent and permit a razor to glide across the skin surface during a shaving process without nicking so as to produce a close shave.

As essential ingredients of the present invention there are included phospholipids, wheat germ oil and at least one fat. Optionally, there is also included jojoba oil. The essential ingredients are admixed with seed and plant or vegetable oils into a blend for a particular use. Advantageously, a composition according to the invention contains about 5–20% by weight of total composition of phospholipid; about 2–15% by weight of total composition of wheat germ oil; 0.5–5% by weight of total composition of at least one fat and the remainder being a mixture of seed and plant or vegetable oils. Jojoba oil in an amount of up to 15% by weight may also be added to improve the shaving performance.

DETAILED DESCRIPTION OF THE INVENTION

The present invention can be broadly defined as a skin conditioning composition having properties which can be utilized in a shaving process. The composition comprises:

A. About 5–20% by weight of total composition of phospholipid;
B. About 2–15% by weight of total composition of wheat germ oil;
C. About 0.5–5% by weight of total composition of at least one fat, and
D. A mixture of seed and vegetable oils which preferably includes jojoba oi of up to about 15% by weight of the mixture.

In a preferred embodiment, the phospholipid is present in an amount of 5–10% by weight of the mixture, the wheat germ oil is present in an amount of 5–10% by weight of the mixture, at least one fat which is derived from the wheat germ oil and lanolin is present in an amount of 0.5–2% of the mixture, jojoba oil is present in an amount of 2–5% by weight of the mixture and the remainder being a combination of seed and vegetable oils. However, mink oil and lanolin oils have also been found to be advantageous in the composition.

Preferred phospholipids for use in the present invention are those which comprise non-saturated fatty acid chains and at least one non-saturated bond. Examples of these non-saturated acids are oleic acid, linoleic acid or linolenic acid. Representative phospholipids of this preferred class are the phosphatidylcholines of which one of the fatty acyl group is from a non-saturated fatty acid.

More generally, reference can be made for the selection of adequate phospholipids to *Phosphatidylcholines-Biochemical and Clinical Aspects of Essential Phospholipids* by H. Peeters, Springer Verlag, Berlin-Heidelberg-New York, 1976, which is incorporated herein by reference. Particularly suitable is lecithin which has been found to provide a moisturizing barrier and the above-skin protective barrier necessary in the shaving process, especially in combination with lanolin wheat gearm oil and/or other seed extracts containing fats and vitamin E.

Among the seed oils which may be utilizied there are included peanut oil, almond oil, safflower oil, cotton seed oil, sesame seed oil, kukui oil, castor oil, sunflower seed oil, avocado oil, apricot oil, soy oil, coconut oil, cocoa butter, and the like.

Among the plant or vegetable oils which may be utilized may be mentioned olive oil, corn oil, aloe oil, jojoba oil, eucalyptus oil, green tea extract, oils from mango, papaya, guava and passion fruit, and the like.

Other ingredients which may be added include lanolin, lanolin oil, mink oil and turtle oil. Preferably, the compositions contain only natural products.

As a preservative it is preferred to utilize natural products such as thyme oil or benzoin extract from plants.

Some of the ingredients which have been found to be entirely absorbed by the hair and skin are safflower oil, sunflower seed oil, coconut oil, olive oil, soy oil, kukui oil, castor oil and mink oil (light).

Some of the ingredients which partially penetrate the hair and skin are sesame oil, cocoa butter (greater penetration when warm), peanut oil, heavy mink oil, wheat germ oil, cotton seed oil, avocado oil and jojoba.

The phospholipids (lecithin) primarily remains on the skin surface to form a barrier which is essential in the shaving process. Wheat germ oil, jojoba oil, lanolin and aloe extracts contain a mixture of fats and oils some of which are absorbed by the hair and skin but the majority remain on the skin surface.

Organic herb extracts some of which contain both oils and fats may also be included in the composition in order to aid in soothing hurting skin. These extracts which are primarily absorbed include fennel extract, hops extract, balm mint extract, mistletoe extract, yarrow extract, ginseng oil, and the like, in amounts depending on whether the composition is primarily for shaving or skin care.

The use of more than one seed and plant or vegetable oil is preferred to obtain a cosolvent effect and a difference in absorption rates between the skin and hair.

An advantage of the composition of the present invention are that they are primarily intended to be non-aqueous so that the composition have a longer shelf-life and do not necessarily require use of preservatives or anit-oxidants, although some of the ingredients have these effects.

The invention is believed to operate in the shaving process as follows:

The penetrating oils and portions of other ingredients are absorbed by the skin and hair. Due to the fact that hair has less or a barrier area, there is greater and more rapid absorption than by the skin. In the absorption process, the voids in and between the skin cells are filled. Because of the difference in absorption rates between the hair and skin, the beard is more quickly set up without oversoftening the skin. The non-penetrating ingredients then provide the glide barrier which permits a quick and highly effective close shave. As a result of the absorption by the beard, the hair follicles are softened so that if they curve around there is no penetration into the skin to cause pseudo folliculitis or as commonly called, "razor bumps".

In a wet shave, that is, one wherein water is an essential ingredient, the skin plumps up greater than with the oils of the invention so that after evaporation of the water there is a stubble showing as a result of the recession of the skin. Also, the hair is not softened so that curving over of the stubble causes penetration by coarse hairs into the skin layer with the result being razor bumps.

The ingredients of the present invention form a long lasting protective barrier by utilizing the barrier properties in and on the skin in a synergistic manner. Thus, the benefits from the composition are greater than one would expect from the individual components. These benefits remain even after shaving. The benefits are even more realized when the party utilizing the composition is in a sauna or steam room since the heat liquifies some of the heavier components and causes their penetration into the skin. The heat also solubilizes some of the waxes and fats by some of the oils and permits absorption into the skin to increase skin conditioning benefits.

Specific examples embodying this invention follow and are not meant to be limiting.

EXAMPLE 1

The following formulation was made and gave a close shave and skin conditioning:

| Ingredient | Percent by Weight |
| --- | --- |
| Lecithin | 5.0 |
| Wheat germ oil | 4.0 |
| Vitamin E | 1.0 |
| Jojoba oil | 2.0 |
| Sesame oil | 18.5 |
| Aloe extract | 0.5 |
| Kukui oil | 6.8 |
| Almond oil | 0.8 |
| Cocoa butter | 0.4 |
| Castor oil | 2.2 |
| Cotton seed oil | 12.0 |
| Peanut oil | 25.5 |
| Olive oil | 9.0 |
| Corn oil | 10.3 |
| Lanolin | 2.0 |

In the above formulation, lecithin may be replaced by any other phsopholipid.

The above formula was tested and found to prevent razor bumps by those individuals having a tendency to develop razor bumps as a result of shaving.

EXAMPLE 2

The following skin conditioning and shaving composition was made and permitted a close shave without the use of soap or water:

| Ingredient | Percent by Weight |
| --- | --- |
| Vitamin E | 5 |
| Lecithin | 12 |
| Wheat germ oil | 8 |
| Jojoba oil | 6 |
| Corn oil | 6 |
| Almond oil | 5 |
| Safflower oil | 4 |
| Sunflower seed oil | 4 |
| Peanut oil | 8 |
| Avocado oil | 5 |
| Olive oil | 10 |
| Coconut oil | 6 |
| Cocoa butter | 8 |
| Aloe | 2 |
| Lanolin | 4 |
| Kukui oil | 1 |

The composition is especially effective when utilized in a sauna or steam room.

It is understood that although the formulation is intended for use without soap, there are individuals who will still desire to combine the formulation with a soap mixture. In such a case, the formulation would be placed on the face and the soap lather applied without rubbing so as not to remove the protective barrier. The combination with soap will permit better cleaning of the razor while shaving. Advantageously, the formulation and a soap preparation can be combined in a bi-container which can conveniently dispense the two compositions.

EXAMPLE 3

The following formulation is intended to condition the face after skiing or prolonged exposure to adverse atmospheric conditions:

| Ingredient | Percent by Weight |
| --- | --- |
| Lecithin | 10 |
| Vitamin E | 2 |
| Wheat germ oil | 5 |
| Jojoba oil | 2 |
| Coconut oil | 4 |
| Cocoa butter | 2 |
| Lanolin oil | 2 |
| Mink oil | 3 |
| Kukui oil | 5 |
| Sweet almond oil | 2 |
| Aloe extract | 1 |
| Fennel extract | 1 |
| Hops extract | 1 |
| Avocado oil | 2 |
| Sesame seed oil | 18 |
| Castor oil | 20 |
| Peanut oil | 20 |
| Olive oil | 10 |
| Para aminobenzoic acid | 3 |
| Thyme oil | 2 |

The formula also provides a clean comfortable shave without using soap or water.

What is claimed is:

1. A substantially non-aqueous conditioning composition consisting essentially of:
   (a) about 5 to 20% by weight of composition of a phospholipid;
   (b) about 0.5 to 5% by weight of composition of vitamin E;
   (c) up to 15% by weight of composition of jojoba oil; and,
   (d) the remainder being a mixture of seed and vegetable oils.

2. The composition of claim 1 wherein the phospholipid is lecithin.

3. The composition of claim 1 including wheat germ oil.

4. The composition of claim 1 including cocoa butter.

* * * * *

UNITED STATES PATENT AND TRADEMARK OFFICE
CERTIFICATE OF CORRECTION

PATENT NO. : 4,784,849
DATED : November 15, 1988
INVENTOR(S) : TUTSKY

It is certified that error appears in the above-identified patent and that said Letters Patent is hereby corrected as shown below:

Column 2, line 35, "oi" should be --oil--.

Column 3, line 43, "anit" should be --anti--.

Column 6, line 15, after "non-aqueous" insert --skin--.

Signed and Sealed this

Twenty-eighth Day of March, 1989

Attest:

DONALD J. QUIGG

Attesting Officer

Commissioner of Patents and Trademarks